United States Patent [19]

Kim

[11] 4,013,734
[45] Mar. 22, 1977

[54] NOVEL CATALYST AND ITS USE FOR STEAM HYDROCONVERSION AND DEALKYLATION PROCESSES

[75] Inventor: Chang J. Kim, Somerset, N.J.
[73] Assignee: Exxon Research and Engineering Company, Linden, N.J.
[22] Filed: May 22, 1975
[21] Appl. No.: 579,867

Related U.S. Application Data

[63] Continuation-in-part of Ser. No. 424,662, Dec. 14, 1973, abandoned.
[52] U.S. Cl. .......................... 260/672 R; 208/124; 208/138
[51] Int. Cl.$^2$ .......................................... C07C 3/58
[58] Field of Search ............... 260/672 R; 208/124, 208/138; 252/464

[56] References Cited

UNITED STATES PATENTS

| | | | |
|---|---|---|---|
| 3,786,001 | 1/1974 | Cornelius et al. | 252/464 |
| 3,799,867 | 3/1974 | Cardwell et al. | 252/464 |
| 3,848,014 | 11/1974 | Uchiyama | 260/672 R |
| 3,898,178 | 8/1975 | Duhaut et al. | 252/464 |

*Primary Examiner*—C. Davis
*Attorney, Agent, or Firm*—Joseph J. Allocca; Ernest A. Forzano

[57] ABSTRACT

A catalyst comprising at least one metal selected from the group consisting of rhodium, palladium, ruthenium, iridium and platinum in combination with a Group VB element supported on a porous carrier is employed in the hydrocracking of heavy aromatic hydrocarbons using steam as the hydrogen source. The product consists mainly of hydrogen, carbon dioxide and lower molecular weight aromatic hydrocarbons. The catalyst is especially useful for the dealkylation of aromatic hydrocarbons.

6 Claims, No Drawings

NOVEL CATALYST AND ITS USE FOR STEAM HYDROCONVERSION AND DEALKYLATION PROCESSES

CROSS-REFERENCE TO RELATED APPLICATION

This application is a continuation-in-part of Ser. No. 424,662 filed Dec. 14, 1973, and now abandoned.

BACKGROUND OF THE INVENTION

The present invention relates to a novel multicomponent catalyst system containing at least one metal selected from the group consisting of rhodium, palladium, ruthenium, iridium and platinum in combination with a Group VB element. In one aspect, this invention involves the use of this catalyst so as to convert heavy feeds into low molecular weight liquid products. In another aspect, the invention relates to methods of producing benzene and its lower molecular weight homologs which are used as a raw material for producing diverse synthetic products. In yet another aspect, the invention relates to the preparation of lower molecular weight homologs via dealkylation of aromatics.

Several processes are available, both catalytic and noncatalytic for the hydrocracking of alkyl aromatic hydrocarbons. These processes generally use hydrogen or steam as a source of hydrogen for the reaction involved, namely, the cleavage of an alkyl group from the aromatic nucleus. Steam is particularly preferred because it is readily available and yields on reaction readily recoverable and valuable hydrogen. In general, catalytic reaction is preferred, since the presence of a catalyst requires less severe reaction conditions, i.e., lower reaction temperatures and lower reaction times, than otherwise available in the absence of catalysts. However, as is characteristic in most catalytic reaction, the catalysts have a tendency to undergo deactivation during the course of processing rendering them less effective than originally and requiring more severe reaction conditions to maintain a constant conversion. Eventually, activity of the catalyst declines to such a level that the processing must be temporarily interrupted to either regenerate or replace the catalyst.

The Russians have described in U.S. Pat. No. 3,595,932 issued July 27, 1971 a process for dealkylating alkyl benzene with steam at a temperature ranging between 380° to 600° C. in the presence of a catalyst. The catalyst is a binary system consisting of platinum, palladium, rhodium, iridium, ruthenium or mixtures thereof deposited in an amount of 0.05 to 5% by weight on a carrier consisting of aluminum oxide, alumino silicate, a combination of aluminum oxide with oxides of nickel or aluminum oxides with oxides of cobalt.

Universal Oil Products Company has also done considerable work in developing steam dealkylation processes in which they use a dual catalyst. In the first zone, they place a nickel component or a Group VIB component as an active catalyst ingredient and then the second zone contains a platinum, palladium or rhodium component as an active catalyst ingredient. Such system is described in U.S. Pat. No. 3,649,707.

In further work, UOP in U.S. Pat. No. 3,649,706 describes a catalyst composite of alumina having combined therewith ferric oxide, alkali metal, chromia and a platinum, palladium or a rhodium component and describes them as being effective steam dealkylation catalyst. They state in this patent that rhodium is the preferred catalyst although the platinum-palladium components are within the scope of the invention.

Furthermore, U.S. Pat. No. 3,436,433 describes a dealkylating process for dealkylating alkyl substituted aromatic hydrocarbons utilizing a rhodium-iron-alkali-metal-chromia-alumina catalyst composite.

The Japanese in a German application No. 2,262,000 describe that the addition of $U_2O_5$ improves significantly the activity of a rhodium-uranium oxide-alumina catalyst in the steam dealkylation of alkylaromatic hydrocarbons. However, one skilled in the art would not be led to believe that a rhodium base catalyst could be improved by the addition of vanadium pentoxide. A three-component catalyst system is significantly different from a two-component catalyst system and this difference would deter a skilled catalyst artisan from concluding that vanadium pentoxide would behave in a similar manner.

Briefly, this invention relates to a catalyst composition comprising a metal, said metal being one selected from the group consisting of rhodium, palladium, ruthenium, iridium, and platinum in combination with a Group VB metal supported on a suitable porous carrier.

The noble metal ranges in an amount from 0.1 to 5.0 wt. % based on the total weight of the catalyst and preferably from 0.3 to 2.0. The Group VB metal ranges from 0.01 to 50 wt. % based on the total weight of the catalyst, preferably from 0.3 to 10, and the porous carrier support makes up the remaining weight of the catalyst.

The porous carrier can be one selected from the group comprising alumina, silica/alumina, silica and kieselguhr. Alumina is the preferred carrier.

The alumina component of the described catalyst is a high surface alumina characterized by a surface area of at least about 10 square meters per gram and preferably a surface area of from about 100 to about 300 square meters per gram. The alumina is suitably prepared by conventional methods described in the art. For example, an alkaline reagent, usually ammonium hydroxide, is added to an aqueous solution of an aluminum salt such as aluminum chloride whereby aluminum hydroxide is precipitated from the solution. Upon washing, drying and calcining at a proper temperature, say from about 450° to about 700° C., the aluminum hydroxide is converted to the desired alumina. The alumina then is impregnated with a solution containing a vanadium compound. The vanadium compound can be vanadium pentoxide, ammonium metavanadate or vanadium oxychloride. After the impregnation with a vanadium compound in a suitable solvent, say aqueous hydrogen peroxide, aqueous HCl, aqueous oxalic acid, or ethanol, the catalyst is dried at a temperature ranging from 60°–120° C. This material is then impregnated with a noble metal salt solution which is then dried at a temperature ranging from 60°–250° C. followed by air calcination at 500° C. for 1 hour. The catalyst is then further reduced with hydrogen gradually increasing the temperature from room temperature to 500° C. over a period of 1 hour and keeping the temperature at 500° C. for 1 hour.

In an alternative method, the alumina can be impregnated with a solution containing both a Group VB compound and a salt of the metal selected from the group consisting of rhodium, palladium, ruthenium, iridium and platinum, hereinafter referred to as a noble metal. Then, the impregnated alumina is dried, calcined and reduced in a similar procedure as described hereinabove.

In a third and preferred method, a Group VB alumina composite was prepared according to procedure described in the first method. This material is then reduced with a suitable reducing agent selected from the group consisting of hydrogen, hydrazine and the like, at 500° C. for 3 hours before impregnating with a noble metal chloride solution. This composite was then dried and reduced as described in the first method.

The steam cracking reaction of this invention is effected by comingling water with a hydrocarbon charge stock in a molar ratio ranging from about 1.0:1 to 20.0:1, preferably 4:1 to 10:1 and heating the mixture in contact with the aforesaid catalyst at a temperature ranging from 300° to 600° C., preferably from 400° to 500° C. The reaction is suitably effected at a pressure ranging from 0 to 1500 psig.

The process is particularly adapted for producing low molecular weight aromatics such as benzene, toluene, xylenes, ethylbenzene at the same time producing hydrogen as a chief by-product. Thus, alkylaromatics, such as toluene, ethylbenzene, xylenes, propylbenzene, methylnaphthalene and the like can be dealkylated or cracked to benzene, toluene, etc., while producing $H_2$. Likewise, condensed ring aromatics such as naphthalene, phenanthrene, anthracene and the like, can be steam-hydrocracked to smaller ring aromatics, such as benzene, toluene, naphthalene, etc., while hydrogen being the principal byproduct. Also, six-membered naphthenes such as alkylcyclohexane, tetralin, decalin, dihydroanthracene and the like, can be effectively dehydroaromatized and cracked to lower molecular weight aromatics such as benzene, toluene, etc., at the same time producing hydrogen as a main byproduct. The said process is also effective in gasifying paraffinic hydrocarbons such as n-heptane, methylcyclopentane, and the like, to mainly hydrogen and carbon oxide at the same time producing low molecular weight aromatics, such as benzene and toluene as chief byproducts.

The said process is also particularly adapted for using hydrocarbon feeds containing nitrogen compounds such as pyridine derivatives, amines and the like. The nitrogen in the feed can be effectively removed in the form of $NH_3$ or $N_2$ without poisoning the said catalysts.

The process of this invention may be effected in either a batch, continuous or semi-continuous type of operation. In the preferred continuous type of operation, the water is preferably converted to steam comingled with the alkyl aromatic hydrocarbon charge in the stated ratio. The mixture may be then preheated and charged to a reactor containing the catalyst disposed in a fixed bed therein. The hydrocarbon is suitably charged to the reactor at a liquid hourly space velocity (LHSV) of from about 0.1 to 10.0, preferably from 1.0 to 5.0. The term "liquid hourly space velocity" as herein employed is defined as a unit of liquid volume of charge in material measured in the state or conditions which are passed per hour through the reaction zone per unit volume of catalyst contained therein. The products of the reaction are conveniently recovered by passing the hot reactor effluent to a condenser separator whereby the normal liquid components are condensed to form an upper hydrocarbon layer and a lower water layer. The noncondensable product such as hydrogen, carbon monoxide, carbon dioxide, methane and so forth being discharged overhead. The hydrocarbon layers continuously separated from the water layers are dried and fractionated to recover the desired product with any unconverted feed being recycled to the reactor as a portion of the hydrocarbon charged thereto. Hydrogen is a principal byproduct of the process of this invention and comprises a substantial portion of the noncondensable product.

EXAMPLE 1

Noble Metal Catalyst Preparation

A noble metal-alumina catalyst was prepared by impregnation techniques by using various noble metal chlorides disposed in an aqueous solution. The alumina was ground to a 20 to 40 mesh size having a surface area of about 100 square meters per gram and was calcined at 500° C. before impregnation with the aqueous solution of the noble metal salts. In the case of ruthenium on alumina and iridium on alumina, the catalyst was dried for several hours at 120° C. and then reduced with hydrogen (1 liter per minute per gram catalyst) gradually increasing the temperature from 25° to 500° C. over a period of one hour and then keeping the temperature at 500° C. for an additional hour. The rhodium/alumina, platinum/alumina, palladium-/alumina catalysts were dried at 120° C., 250° C. and calcined at 500° C. under air flow for one hour followed by similar reduction treatment described for the ruthenium and iridium catalysts. The metal surface areas of these catalysts thus prepared were determined by the hydrogen chemisorption measurements. The following catalysts were thus characterized.

TABLE I

| Catalyst No. | Catalyst (Wt. % Metal) | % Metal Dispersion Determined by $H_2$ Chemisorption[a] |
|---|---|---|
| 1 | 0.6 Rh/AlO$_3$ | 100 |
| 2 | 0.6 Pd/AlO$_3$ | 81 |
| 3 | 0.6 Pt/AlO$_3$ | 100 |
| 4 | 0.6 Ru/AlO$_3$ | 100 |
| 5 | 0.6 Ir/AlO$_3$ | 100 |

[a]Percent metal on the surface of support capable of adsorbing hydrogen.

EXAMPLE 2

Rhodium-Vanadium Catalysts

The vanadium component was introduced by using a variety of vanadium compounds, such as $V_2O_5$ (in aqueous $H_2O_2$ or in HCl solution), $NH_4VO_3$ (in aqueous oxalic acid or in aqueous $H_2O_2$ solution) and $VOCl_3$ (ethanol solution). The rhodium component was introduced as $RhCl_3 \cdot xH_2O$. Three different procedures were employed, which are described as follows.

Method A.

Alumina (20-40 mesh granules) was impregnated with an ethanol solution containing vanadium oxychloride. The composite was dried successively, first at a temperature of 60° and then at 120°. This material was then impregnated with an aqueous rhodium chloride solution, dried at 60°, 120° and 250° C. followed by air calcination at 500° C. for 1 hour. This catalyst was reduced with $H_2$, gradually increasing the temperature from room temperature to 500° C. over a period of 1 hour and keeping the temperature at 500° C. for 1 hour.

Method B.

Alumina was impregnated with a solution containing both a vanadium compound and the rhodium compound followed by similar drying, air calcination and reduction procedure described in Method A.

Method C.

A vanadium-alumina composite was prepared by impregnating alumina with an appropriate solution containing a vanadium compound, and by drying successively at 60°, 120° and 250° C. This composite was then calcined in air at 500° for 2 hours, cooled to room temperature, and then hydrogen was introduced (1 liter per minute per 40 gram of catalyst) to raise the temperature gradually to 500° C. over a period of 1 hour and further reduced at 500° C. for 3 hours. This material was impregnated with a rhodium trichloride solution, dried at 60° and at 120° C., followed by a similar reduction procedure described in Method A.

TABLE II

| Catalyst No. | Method of Preparation | Vanadium Precursor | Catalyst (Wt. % as Metal) | % Dispersion of Rh from $H_2$ Chemisorp. |
|---|---|---|---|---|
| 6 | A | $VOCl_3$ | 0.6 Rh/2.4V/$Al_2O_3$ | |
| 7 | A | $VOCl_3$ | 1.35 Rh/2.4V/$Al_2O_3$ | 62 |
| 8 | B | $NH_4VO_3$ | 0.6 Rh/1.2V/$Al_2O_3$ | |
| 9 | B | $V_2O_5$ | 0.6 Rh/0.6V/$Al_2O_3$ | 85 |
| 10 | B | $V_2O_5$ | 0.6 Rh/0.3V/$Al_2O_3$ | |
| 11 | B | $VOCl_3$ | 0.6 Rh/0.3V/$Al_2O_3$ | |
| 12 | B | $V_2O_5$ | 0.6 Rh/0.1V/$Al_2O_3$ | |
| 13 | C | $NH_4VO_3$ | 0.6 Rh/5.6V/$Al_2O_3$ | 69 |

EXAMPLE 3

Rhodium-Niobium, Rhodium-Tantalum, and Other Catalysts

A catalyst composite containing 0.6 wt. % rhodium and 1.1 wt. % niobium on alumina (Catalyst No. 14) was prepared by impregnating alumina, ground to 20-40 mesh size and previously calcined at 500° C., with an ethanol solution containing $RhCl_3.3H_2O$ and $NbCl_5$. After drying at room temperature, the material was wetted with a small amount of water, dried successively at 60° C., 120° C. and 250° C., followed by air calcination and reduction with $H_2$ according to the general procedure described in Example 2, Method A.

A 0.6 Rh/2 Ta/$Al_2O_3$ composite (Catalyst No. 15) was prepared in an essentially same way described above.

A 0.3 Rh/0.3 Pt/$Al_2O_3$ catalyst (Catalyst No. 16) was obtained by following the procedure specified in U.S. Pat. No. 3,595,932.

Another patented catalyst, 0.6 Rh/10 $Cr_2O_3$/2 $K_2O$/1 $Fe_2O_3$/$Al_2O_3$ (Catalyst No. 17), was prepared by exactly copying the procedure described in U.S. Pat. No. 3,649,706.

EXAMPLE 4

Quantitative Determination of Activities of Various Catalysts

Rate measurements in use of a differential reactor technique represent a standard means of evaluating activities of catalysts. The rate is expressed in terms of turnover number which should be familiar to those involved in the art of catalysis. Turnover number is usually defined as number of molecules of reactant converted per active site on the catalyst per unit time, and this quantity can be directly used in evaluating catalyst performance. For the purpose of rating the catalysts prepared in Examples 1, 2 and 3, water-toluene reaction was chosen as a model reaction and rates determined at various temperatures.

In each run, a particular catalyst was ground to 60—80 mesh powder, and a measured amount in the range of 0.2-1.0 grams was charged in a micro fixed bed flow reactor. A thermocouple was directly inserted into the catalyst bed, and the catalyst was reduced at 500° C. for 1 hour before run. Water and hydrocarbon feed were pumped into the reactor at rates of 1.31 gr./hr. and 1.73 gr./hr., respectively. At a preset temperature the reaction products were analyzed after 30 minutes from the start of feeds. In a given run, this operation was performed at several different temperatures, which establishes a reliable temperature-rate correlation (Arrehnius plot). In this patent the rate will be expressed in terms of moles of benzene produced per gram atom of noble metal present in the bed per second. This treatment does not count the effect of dispersion but directly relates the actual performance of a particular batch of catalyst. Considerations on the effect of dispersion will be noted later in this example. The results are shown in Table IV.

TABLE III

RELATIVE ACTIVITIES OF VARIOUS CATALYSTS IN WATER-TOLUENE REACTION AT 400° C.

| No. | Catalyst Wt. % as Metal on $Al_2O_3$ | Rate[a] | Relative Activity of Catalyst |
|---|---|---|---|
| 1 | 0.6 Rh | 0.0134 | 1.0 |
| 2 | 0.6 Pd | 0.0062 | 0.46 |
| 3 | 0.6 Pt | 0.0035 | 0.26 |
| 4 | 0.6 Ru | 0.0020 | 0.15 |
| 5 | 0.6 Ir | 0.0015 | 0.11 |
| 16 | 0.3 Rh/0.3Pt | 0.018 | 1.3 |
| 17 | 0.6 Rh/Cr-K-Fe | 0.010 | 0.75 |
| 13 | 0.6 Rh/5.6 V | 0.043 | 3.2 |
| 8 | 0.6 Rh/1.2 V | 0.027 | 2.0 |
| 9 | 0.6 Rh/0.6 V | 0.035 | 2.6 |
| 10 | 0.6 Rh/0.3 V | 0.026 | 1.9 |
| 11 | 0.6 Rh/0.3 V | 0.030 | 2.2 |
| 12 | 0.6 Rh/0.1 V | 0.022 | 1.6 |
| 7 | 1.35 Rh/2.4 V | 0.021 | 1.5 |
| 14 | 0.6 Rh/1.1 Nb | 0.016 | 1.2 |
| 15 | 0.6 Rh/2 Ta | 0.018 | 1.3 |

[a]Moles of benzene produced/g atoms noble metal (total)/sec.

Among the platinum metal catlysts (excluding Os), rhodium has the highest activity and iridium the lowest, the activity being an order of magnitude lower than rhodium. The Russian catalyst 0.3 Rh/0.3 Pt/$Al_2O_3$ was found to be indeed substantially more active than a 0.6 Rh catalyst. The UOP catalyst 0.6 Rh/Cr—K—Fe/$Al_2O_3$, on the other hand, is less active than a 0.6 Rh/$Al_2O_3$ catalyst.

Catalysts containing Group VB element and Rh show high activities in all cases. Vanadium is especially effective in this connection. By introducing a suitable amount of vanadium by a suitable procedure into a rhodium-alumina catalyst, the activity jumps by a factor of 1.5 – 3.2. In fact, the true activities of these Rh-V/$Al_2O_3$ catalysts are even higher, because $H_2$ chemisorption measurements showed that rhodium in these catalysts are not fully dispersed (see Table II). Taking account of this fact, the activities of Rh-V/Al$_2$O$_3$ catalysts are 2.3 – 4.5 folds higher than a Rh/Al$_2$O$_3$ catalyst. It is noted here that a vanadium/Al$_2$O$_3$ catalyst is essentially inactive in the reaction under consideration. Therefore, the present rhodium-vanadium system represents a novel combination in which synergetic interaction is evident.

EXAMPLE 5

Some of the catalysts prepared in Examples 1, 2, and 3 were examined here under the following condition which allows a high level of feed conversion. This was intended to evaluate catalyst performance under a practical condition.

TABLE IV

WATER-TOLUENE REACTION

Amount of Catalyst used: 1.6 grams (ca. 2.0 ml in bulk volume)
Toluene feed rate: 2.0 ml/hr.
H$_2$O/Tol mole ratio: 3.9
Pressure: Atmospheric

| No. | Wt. % on Al$_2$O$_3$ | Temperature, ° C. | Total Conversion % | Yield Benzene % | Selectivity to Benzene % |
|---|---|---|---|---|---|
| 1 | 0.6 Rh | 460 | 65 | 57 | 88 |
| 16 | 0.3 Rh/0.3 Pt | 460 | 69 | 62 | 90 |
| 17 | 0.6 Rh/Cr-K-Fe | 460 | 45 | 40 | 88 |
| 13 | 0.6 Rh/5.6 V | 460 | 89 | 74 | 83 |
|  |  | 400 | 55 | 51 | 93 |

EXAMPLES 6–17

In Examples 6–17, the reactions of water with various types of hydrocarbon feeds were examined in use of a micro fixed bed flow reactor. For this purpose, the 1.35 Rh/2.4 V/Al$_2$O$_3$ catalyst (Catalyst No. 7) was chosen, and the following standard conditions were employed:
  Temperature: 480° C. (unless noted otherwise)
  Pressure: Atmospheric
  Hydrocarbon liquid feed rate: 4 ml/hr.
  Water liquid feed rate: 4 ml/hr.
  Amount of catalyst used per run: 1.6 gr (2.0 ml)
  Carried gas flow rate: 1.3 l/hr
  Duration of a run: 2 hrs.

EXAMPLE 6

Under the standard conditions described above, toluene reacts with water giving 92.7% total conversion and 79% selectivity to benzene. The exit gas was composed of 63% H$_2$, 26% CO$_2$, 5% CO, 6% CH$_4$ and 0.2% C$_2$H$_6$.

EXAMPLE 7

Under the standard conditions, n-heptane undergoes 76% conversion, mainly to gaseous products. Per mole of feed converted, there were obtained 0.09 mole of benzene and 0.06 mole of toluene besides the gases. The exit gas was composed of 61% H$_2$, 26% CO$_2$, 6% CO, 7% CH$_4$, and 0.4% C$_2$H$_6$.

EXAMPLE 8

Under the standard condition, methylcyclohexane converts essentially quantitatively to give 73% benzene, 14% toluene and the rest to gases. The exit gas was composed of 80% H$_2$, 13% CO$_2$, 5% CO, and 2% CH$_4$.

EXAMPLE 9

Under the standard condition, diphenylmethane undergoes 64% conversion, mainly to benzene, toluene, and gases. Per mole of feed converted there formed 0.64 mole of benzene and 0.20 mole of toluene. The exit gas was composed of 68% H$_2$, 26% CO$_2$, 5% CO and 2% CH$_4$.

EXAMPLE 10

The reaction of diphenylethane with water, under the standard condition, gives a total conversion level of the feed at 79%. Per mole of feed converted, there were obtained 0.89 mole of benzene, 0.36 mole of toluene, and a combined total of 0.21 mole of higher boiling aromatics which include naphthalene, diphenylmethane, stilbene, penanthrene, etc. The gaseous product stream contained 68% H$_2$, 27% CO$_2$, 4% CO, and 1% CH$_4$.

EXAMPLE 11

Tetralin (1,2,3,4-tetrahydronaphthalene) reacts quantitatively with water under the standard condition to give 22% benzene, 6% toluene, 67% naphthalene, and the rest to gases. The exit gas composition was 77% H$_2$, 19% CO$_2$, 3% CO, and 2% CH$_4$. By raising the reaction temperature to 550° C., the yield of benzene increases to 49%, while the amount of naphthalene decreases to 10%.

EXAMPLE 12

Reaction of naphthalene with water, under the standard condition, proceeds with a 40% conversion level, the selectivities being 56% to benzene, 12% to toluene, and 30% to gaseous products. The exit gas composition was 64% H$_2$, 29% CO$_2$, 4% CO, and 2% CH$_4$. At 540° C., the conversion rises to 74%, the selectivity remaining largely unchanged.

EXAMPLE 13

Under the standard reaction condition, 9,10-dihydropenanthrene converts quantitatively, 59% to phenanthrene, 27% to naphthalene, 4% to benzene, 1% to toluene, 6% to gaseous products, and 3% to others. The exit gas was composed of 71% H$_2$, 25% CO$_2$, 3% CO, and 1% CH$_4$. By raising the reaction temperature to 540°, while keeping other variables constant, the selectivities become 38% to phenanthrene, 35% to naphthalene, 12% to benzene, 2% to toluene, 8% to gases, and 5% to other products. The exit gas was composed of 68% H$_2$, 23% CO$_2$, 9% CO, and 0.2% CH$_4$.

EXAMPLE 14

Methylcyclopentane reacts smoothly with water under the standard reaction condition undergoing 59% conversion. The selectivity pattern was 81% to gaseous products, 14% to benzene, and 4% to toluene. The exit gas composition was 62% $H_2$, 21% $CO_2$, 6% CO, 9% $CH_4$, and 2% $C_2H_6$.

EXAMPLE 15

Under the standard condition, the reaction of n-propylbenzene with water occurs with 68% conversion of the hydrocarbon feed. Per mole of feed converted, there were obtained 0.37 mole of benzene, 0.34 mole of toluene, and 0.14 mole of ethylbenzene. The exit gas was composed of 64% $H_2$, 25% $CO_2$, 4% CO, 5% $CH_4$, and $C_2H_6$.

EXAMPLE 16

4-Picoline (4-methylpyridine) reacts readily with water under the standard condition undergoing 46% conversion of feed, mainly to gaseous products. The selectivities are 70% to gases ($H_2$, $CO_2$, CO, $CH_4$, and $NH_3$), 18% to pyridine, and 10% to lutidines (dimethylpyridines). The exit gas after a dry-ice trap was composed of 55% $H_2$, 29% $CO_2$, 9% CO, and 7% $CH_4$. Ammonia, which undergoes partial decomposition to $H_2$ and $N_2$ under this condition, was trapped in the liquid receiver.

EXAMPLE 17

A refinery feed, a naphtha fraction containing about 7% of $C_6$–$C_8$ aromatics, as well as about 50% of $C_9^+$ fraction, was reacted with water under the standard condition (temperature; variable; duration of a run: 4.0 hours). At 480° C., the liquid yield was 67 wt. % of the feed input which contained 43 wt. % of $C_6$–$C_8$ aromatics, and 23 wt. % of $C_9^+$ fraction. The exit gas was composed of 72% $H_2$, 20% $CO_2$, 4% CO, 4% $CH_4$, and 0.3% $C_2H_6$. At 550° C., the liquid yield becomes 24 wt. % of feed. This is composed of mainly $C_6$–$C_8$ aromatics (76%) and a greatly decreased amount of heavier $C_9^+$ fraction (7%). The exit gas composition was 60% $H_2$, 14% $CO_2$, 10% CO, 15% $CH_4$, and 0.2 % $C_2H_6$. (cf. Table V).

TABLE V
REACTION OF WATER WITH A NAPHTHA FEED OVER A Rh-V/$Al_2O_3$ CATALYST

| Condition: see text. | | | | |
|---|---|---|---|---|
| Temperature | | 480° C. | | 550° C. |
| Liquid Yield, wt. % | | 67 | | 24 |
| Liquid Composition: | Feed | — | Product | — |
| Benzene | 0.3 | 14.1 | | 56.6 |
| Toluene | 2.2 | 18.0 | | 15.5 |
| $C_8$ Aromatics | 4.2 | 10.7 | | 3.7 |
| $C_9$ + Fraction | 50.7 | 22.8 | | 6.8 |

What is claimed is:

1. A hydrocarbon conversion process which comprises comingling water with said hydrocarbon in a molar ratio ranging from 1.0:1 to 20.0:1, heating the mixture at a temperature of from 300° to 600° C., at a pressure of from 0–1500 psig, in contact with a catalyst composition consisting of a Group VIII metal selected from the group consisting of rhodium, palladium, ruthenium, iridium and platinum in combination with a Group VB element, said Group VB element and metal being deposited on an alumina support.

2. A process according to claim 1 wherein said hydrocarbon is an aromatic compound.

3. A process according to claim 1, wherein said hydrocarbon is a hydrocarbon mixture containing $C_6^+$ fraction.

4. A process according to claim 1, wherein said hydrocarbon contains nitrogen compounds.

5. A process according to claim 1 wherein said hydrocarbon conversion process is a dealkylation process.

6. A process according to claim 1 characterized in that the Group VIII metal is present in the range of 0.1 to 5.0 wt. %; the Group VB metal is present in the range of 0.01 to 50.0 wt. %; the balance being alumina support.

* * * * *